United States Patent [19]

Ona et al.

[11] 4,450,152

[45] May 22, 1984

[54] COMPOSITION USED TO GROOM HAIR

[75] Inventors: Isao Ona; Asao Harashima; Masaru Ozaki; Yoichiro Taki, all of Chiba, Japan

[73] Assignee: Toray Silicone Company, Ltd., Tokyo, Japan

[21] Appl. No.: 386,860

[22] Filed: Jun. 10, 1982

[30] Foreign Application Priority Data

Oct. 29, 1981 [JP] Japan .................. 56-173253

[51] Int. Cl.³ .................. A61K 7/06; A61K 7/08; A61K 7/15
[52] U.S. Cl. .................. 424/70; 424/DIG. 5; 424/47; 424/73; 424/184; 424/358; 424/365
[58] Field of Search .................. 424/70, 184

[56] References Cited

U.S. PATENT DOCUMENTS 4,342,742 8/1982 Sebag et al. .................. 424/184

FOREIGN PATENT DOCUMENTS 55-66506 5/1980 Japan .................. 424/70
2058103 4/1981 United Kingdom .................. 424/70

Primary Examiner—Dale R. Ore
Attorney, Agent, or Firm—James E. Bittell

[57] ABSTRACT

A composition, used to groom hair, consisting essentially of an organopolysiloxane having at least one alkylamino substituent and at least one substituent selected from the group consisting of oxyalkylene, polyoxyalkylene, and hydroxyalkyl groups, said organopolysiloxane having a viscosity range of 1 to 100,000 centistokes at 25° C., is disclosed.

4 Claims, No Drawings

COMPOSITION USED TO GROOM HAIR

FIELD OF THE INVENTION

This invention relates to a composition, used to groom hair, consisting essentially of an organopolysiloxane having at least one alkylamino substituent and at least one substituent selected from the group consisting of oxyalkylene, polyoxyalkylene, and hydroxyalkyl groups, said organopolysiloxane having a viscosity range of 1 to 100,000 centistokes at 25° C.

DESCRIPTION OF THE PRIOR ART

Hair is easily damaged mechanically by combing, brushing, and washing. Hair is also easily damaged physically and chemically by the sun, hair dryers, and permanents. In order to protect the hair, vegetable oils such as camellia oil and olive oil, animal oils such as lanolin and beef tallow, mineral oils such as vaseline and paraffin, and synthetic oils have been used either directly, as emulsions, or dissolved in solvents.

In recent years, organopolysiloxane has attracted attention as a hair grooming agent because it gives hair glossiness, suppleness, smoothness, and a moist feeling. For example, a hair dressing composed of dimethylpolysiloxane and diol derivatives or a branched aliphatic alcohol is disclosed in U.S. Pat. No. 4,243,657; a hair conditioning composition composed of a polyorganosiloxane-polyoxyalkylene block copolymer and aqueous or anhydrous ethanol is disclosed in Japanese Pat. No. Sho. 56[1980]-136214; a hair grooming agent composed of (alkylamino)methylpolysiloxane and a cationic surfactant with an aqueous carrier is disclosed in Great Britain Pat. No. 2,058,103; and a dressing which uses a cationic modified organopolysiloxane containing quaternary nitrogen is disclosed in Japanese Pat. No. Sho 55[1980]-66506.

Hair grooming agents in which dimethylpolysiloxane is used have the drawback, however, in that dust tends to stick to the hair and the flying phenomenon easily occurs because of the generation of static electricity. Those in which organopolysiloxane-polyoxyalkylene block copolymers are used are able to prevent the generation of static electricity, but have the drawbacks that they are easily removed when swimming or washing the hair because they are easily dissolved in water. Those in which (alkylamino)methylpolysiloxane is used are ideal in terms of their durability, but have the drawback that static electricity is easily generated. Those in which cationic modified organopolysiloxane containing quaternary nitrogen is used are fairly good in both their durability and antistatic properties, but have the drawback in that those qualities alone are insufficient. Thus, in the case of conventional hair grooming agents, even though they generally succeed in giving glossiness, suppleness, smoothness, and a moist feeling, they have problems with durability and antistatic properties, so a grooming agent in which the treatment effects, the durability, and the antistatic properties are fully satisfactory, has not yet been obtained.

As a result of intensive investigations to improve the above-mentioned drawbacks, the present inventors have succeeded in developing a hair grooming agent which gives the hair an excellent glossiness, suppleness, smoothness, and moist feeling, making it easy to brush and providing it with antistatic properties, and which moreover has a durability that can make the treatment effects adequately durable because it is adsorbed onto the hair.

That is, the present invention relates to a composition, used to groom hair, consisting essentially of an organopolysiloxane having at least one alkylamino substituent and at least one substituent selected from the group consisting of oxyalkylene, polyoxyalkylene, and hydroxyalkyl groups, said organopolysiloxane having a viscosity range of 1 to 100,000 centistokes at 25° C.

It is thus an object of this invention to provide a composition used for grooming hair which is adsorbed onto the hair and which gives it a durable gloss, suppleness, smoothness, and a moist feeling, making it easy to brush and providing it with antistatic properties.

DETAILED DESCRIPTION

This invention relates to a composition, used to groom hair, consisting essentially of an organopolysiloxane having at least one alkylamino substituent and at least one substituent selected from the group consisting of oxyalkylene, polyoxyalkylene, and hydroxyalkyl groups, said organopolysiloxane having a viscosity range of 1 to 100,000 centistokes at 25° C.

It is believed that the organopolysiloxane imparts glossiness, suppleness, smoothness, and a moist feeling onto the hair. The molecular configuration of the organopolysiloxane is not critical for the purpose of this invention and therefore may be either a straight chain, a branched chain, a cyclic, or a branched chain network. It is preferred, however, that the configuration be a straight chain.

By means of the alkylamino groups bonded to the silicon atoms which firmly adsorbs on the hair, it is believed that durability is achieved. It is essential that the organopolysiloxane have at least one alkylamino substituent in order to achieve this durability. A suitable example of the alkylamino groups is represented by the general formula

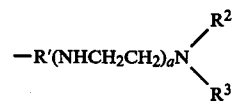

wherein R' is a divalent hydrocarbon group, R² and R³ are selected from the group consisting of hydrogen and monovalent hydrocarbon groups, and a has a value of 0 to 5. Examples of the divalent hydrocarbon group, R', include alkylene groups such as methylene, ethylene, propylene, isobutylene and butylene, and alkylenearylene groups such as —(CH$_2$)$_2$C$_6$H$_4$. It is preferred that R' be an alkylene group, with propylene being the most preferred. Examples of the monovalent hydrocarbon groups, R² and R³, are alkyl groups such as methyl, ethyl, propyl, and hexyl, and aryl groups such as phenyl. It is further preferred that a have a value of 0 to 1.

It is believed that the organopolysiloxane substituent selected from the group consisting of oxyalkylene, polyoxyalkylene, and hydroxyalkyl groups prevents the generation of static electricity and bestows wettability, due to their hydrophilic character. A suitable example of the oxyalkylene and polyoxyalkylene groups is represented by the general formula

wherein $R^4$ is a divalent hydrocarbon group, $R^5$ is selected from the group consisting of hydrogen and end-blocking groups, b has a value of 0 to 1, m has a value of 1 to 5 and c has a value of 1 to 100. Examples of the divalent hydrocarbon group, $R^4$, include alkylene groups such as methylene, ethylene, propylene, isobutylene and butylene, and alkylenearylene groups such as —$(CH_2)_2C_6H_4$. It is preferred that $R^4$ be an alkylene group. The end-blocking group, $R^5$, is represented by monovalent hydrocarbons, acyls, and, carbonic acid monoester groups. Specific examples of the monovalent hydrocarbon group include alkyl groups such as methyl, ethyl, hexyl, and propyl, and aryl groups such as phenyl. The acyl group is represented by the acetyl, propionyl, and benzoyl groups. It is preferred that b have the value of 1, m have the value of 2 to 3, and c have the value of 3 to 70. A suitable example of the hydroxyalkyl group is expressed by the general formula —$R^4OH$ wherein $R^4$ is a divalent hydrocarbon group. Examples of the divalent hydrocarbon group, $R^4$, include alkylene groups such as methylene, ethylene, propylene, isobutylene and butylene, and alkylenearylene groups such as —$(CH_2)_2C_6H_4$. It is preferred that $R^4$ be an alkylene group. It is further preferred that the organopolysiloxane substituent selected from the group consisting of oxyalkylene, polyoxyalkylene, and hydroxyalkyl groups, be a polyoxyalkylene, with the second preference being oxyalkylene, and the third, hydroxyalkyl.

Groups other than those mentioned above which constitutes the organopolysiloxane include alkyl groups such as methyl, ethyl, propyl, octyl, and dodecyl groups, aryl groups such as phenyl and tolyl groups, cycloalkyl groups such as cyclohexyl and cycloheptyl groups, and substituted alkyl groups such as 2-phenylethyl, 3,3,3-trifluoropropyl, and 3-chloropropyl groups. Among these, the methyl group is the most common. Hydroxyl and alkoxy groups which are directly attached to the silicon atoms may also be present.

The organopolysiloxane of the present invention can be prepared by techniques well known to those skilled in the art. A suitable method is one of reacting an organopolysiloxane which contains alkylamino groups with an organopolysiloxane which contains oxyalkylene, polyoxyalkylene, or hydroxyalkyl groups in the presence of an alkaline catalyst. Another method is reacting ammonia or an alkylamine with an organopolysiloxane which contains oxyalkylene, polyoxyalkylene, or hydroxyalkyl groups as well as monohalogenated alkyl groups. A further method is the condensation reaction of a dialkoxysilane containing aminoalkyl groups with a dialkoxysilane containing oxyalkylene, polyoxyalkylene, or hydroxyalkyl groups in the presence of a silanol endblocked diorganopolysiloxane.

The quantity of the organopolysiloxane of the present invention that is used, will vary according to its intended application, but is usually employed in the range of 0.01 to 10 percent by weight with respect to the total quantity of the hair care agent. The organopolysiloxane can be used as is, dissolved in an aqueous solution or an organic solvent, or employed as an emulsion. Besides the organopolysiloxane, the hair care agent may also contain additives used in cosmetics and sprays. Conventional cosmetic additives include surfactants; organic solvents such as alcohols, esters, ketones, and aromatics; perfumes; inorganic pigments; coloring agents; thickeners; animal fats and oils; vegetable fats and oils; mineral fats and oils; ultraviolet ray absorbants; antioxidants; antiseptics; appearance-changing additives; and other organopolysiloxanes. Conventional spray additives includes spray agents such as LPG, trichloromonofluoromethane, dichlorodifluoromethane, dichlorotetrafluoroethane and carbonic acid gas.

The organopolysiloxane of the present invention can be used in shampoos, rinses, hair cremes, hair oils, hair lotions, liquid or solid pomades, stick pomades, shaving foams, and skin ointments such as skin creams, shaving creams, and skin lotions.

Hair, as used in the present invention, refers to the hair of the head, other humain hair, artificial hair such as wigs, and animal hair such as that of dogs, cats and sheep.

Now in order that those skilled in the art may better understand the invention, the following examples are given by way of illustration and not by way of limitation. All parts referred to herein are by weight, and all viscosities are measured at 25° C., unless otherwise specified.

EXAMPLE 1

Hair grooming agents were prepared and evaluated on hair in terms of imparting glossiness, suppleness, smoothness, moist feeling, ease of brushing, and difficulty of dust adhesion. The hair grooming agent consists of 4 parts by weight of an organopolysiloxane, 16 parts by weight of ethanol, a small amount of artificial perfume, 40 parts by weight of trichloromonofluoromethane, and 40 parts by weight of dichlorodifluoromethane. The agent is then placed in an aerosol-type spray can and sprayed uniformly onto the hair of a woman's head, having a hair length of about 25 centimeters. The hair was brushed 100 times with a brush made of polyethylene, and the ease of brushing, glossiness, suppleness, smoothness, and moist feeling were evaluated by means of a sensory inspection. The reporting system of the evaluation was a scale of 1 to 4 with 1 being extremely good, 2 being fairly good, 3 being fairly poor, and 4 being extremely poor. The ease with which dust stuck to the hair immediately after brushing, due to the generation of static electricity, was also evaluated. This was done by preparing a large number of very small pieces of paper, blowing them on the hair immediately after brushing, and evaluating according to the number of pieces of paper absorbed onto the hair. The evaluation scale was also 1 to 4, with 1 indicating almost no adhesion, 2, some adhesion, 3, moderate adhesion, and 4 abundant adhesion.

The organopolysiloxanes of the present invention used in the hair grooming agent are as follows:
Composition 1, having a viscosity of 4000 centistokes at 25° C.:

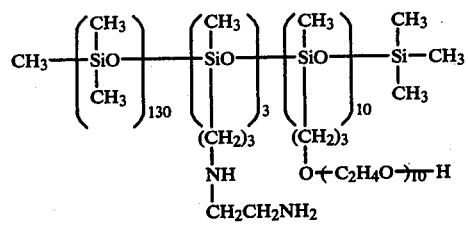

Composition 2, having a viscosity of 400 centistokes at 25° C.:

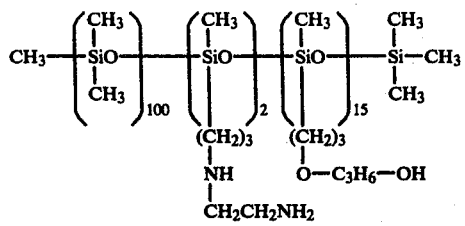

Composition 3, having a viscosity of 200 centistokes at 25° C.:

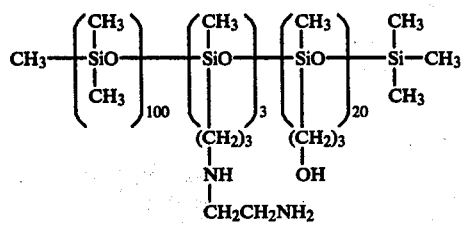

Organopolysiloxanes, serving as comparisons, used in the hair grooming agent are as follows:

Comparison Composition 1, having a viscosity of 100 centistokes at 25° C.:

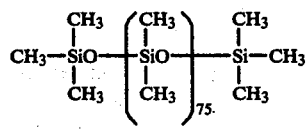

Comparison Composition 2, having a viscosity of 1100 centistokes at 25° C.:

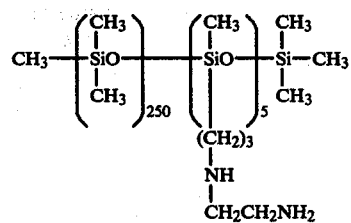

and Comparison Composition 3, having a viscosity of 350 centistokes at 25° C.:

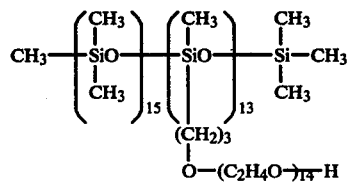

The results are as follows:

| Item | Composition | | | Comparison Composition | | |
|---|---|---|---|---|---|---|
| | 1 | 2 | 3 | 1 | 2 | 3 |
| Glossiness | 1 | 1 | 1 | 2 | 1 | 2 |
| Suppleness | 1 | 1 | 1 | 2 | 2 | 2 |

-continued

| Item | Composition | | | Comparison Composition | | |
|---|---|---|---|---|---|---|
| | 1 | 2 | 3 | 1 | 2 | 3 |
| Smoothness | 1 | 1 | 1 | 1 | 3 | 1 |
| Moist Feeling | 1 | 1 | 1 | 3 | 3 | 1 |
| Ease of Brushing | 1 | 1 | 2 | 3 | 3 | 2 |
| Difficulty of Dust Adhesion | 1 | 2 | 2 | 4 | 4 | 1 |

As shown in the above results, it was found that the organopolysiloxanes of the present invention were considerably superior to the conventionally well known organopolysiloxanes which were used in the comparison compositions. In the present invention, it is clear that the polyoxyalkylene substituent is superior to the oxyalkylene substituent which is superior to the hydroxyalkyl substituent, as shown in the results in ease of brushing and difficulty of dust adhesion. Though Comparison Composition 3 is not greatly different from those of the present invention, as shown in the results, it is extremely inferior to the present invention in terms of durability as shown in Example 2.

EXAMPLE 2

The durability of organopolysiloxanes in hair grooming agents was tested by immersing 20 grams of a lock of woman's hair, approximately 15 centimeters in length, in a hair grooming agent consisting of 4 parts by weight of an organopolysiloxane, and 96 parts by weight of n-pentane. After a 30 minute immersion, the hair was removed, and after it ceased dripping, was dried with a hair dryer. This lock of hair was then washed while being lightly massaged for 15 minutes in a 0.1 percent by weight aqueous solution of potassium soap used for babies which had been warmed to 45° C. The hair was then rinsed with water and dried. The quantity of organopolysiloxane adhering after shampooing was measured using an X-ray fluorescence apparatus manufactured by Rigaku Denki Kogyo. The quantity adhering was expressed as an organopolysiloxane residue ratio with the quantity adhering before shampooing regarded as 100. Sensory inspection and evaluation before and after shampooing was carried out in the same manner as in Example 1.

The organopolysiloxane of the present invention used in the hair grooming agent is:

Composition 4, having a viscosity of 8500 centistokes at 25° C.:

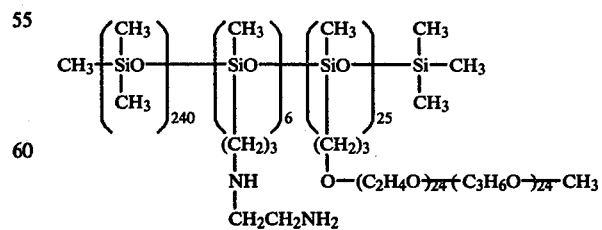

Organopolysiloxanes, serving as comparisons, used in the hair grooming agent are as follows:

Comparison Composition 4, having a viscosity of 100 centistokes at 25° C.:

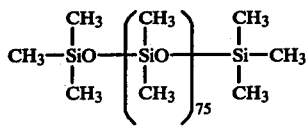

and Comparison Composition 5, having a viscosity of 350 centistokes at 25° C.

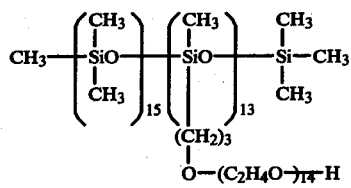

The results are as follows:

| Item | Composition 4 | Comparison Composition 4 | Comparison Composition 5 |
|---|---|---|---|
| Before shampooing | | | |
| Glossiness | 1 | 2 | 2 |
| Suppleness | 1 | 2 | 2 |
| Smoothness | 1 | 1 | 1 |
| Moist Feeling | 1 | 3 | 1 |
| After shampooing | | | |
| Glossiness | 1 | 3 | 4 |
| Suppleness | 2 | 3 | 3 |
| Smoothness | 1 | 3 | 4 |
| Moist Feeling | 2 | 4 | 4 |
| Organopolysiloxane Residue Ratio (%) | 38 | 11 | 4 |

It was found that the organopolysiloxane of the present invention, as indicated by Composition 4, had a high ratio of organopolysiloxane remaining, even after shampooing 3 times, because it was firmly adsorbed onto the hair, and consequently its effects upon the hair were retained, imparting an excellent durability. By contrast, the effects on the hair before washing in the case of Comparison Composition 5 were not greatly different from the present invention, but its effects upon the hair after shampooing largely disappeared, and its durability was inferior.

That which is claimed is:

1. A hair grooming composition consisting essentially of 0.01 to 10 percent by weight of an organopolysiloxane having at least one alkylamino substituent having the general formula $$-R'(NHCH_2CH_2)_a NR^2 R^3$$

wherein $R'$ is a divalent hydrocarbon group, $R^2$ and $R^3$ are selected from the group consisting of hydrogen and monovalent hydrocarbon groups, and a has a value of 0 to 5 and at least one substituent selected from the group consisting of oxyalkylene, polyoxyalkylene, and hydroxyalkyl groups, the oxyalkylene and polyoxyalkylene substituents having the general formula $$-R_b^4 O(C_m H_{2m} O)_c R^5$$

wherein $R^4$ is a divalent hydrocarbon group, $R^5$ is selected from the group consisting of hydrogen and endblocking groups, b has a value of 0 to 1, m has a value of 1 to 5, and c has a value of 1 to 100, and the hydroxyalkyl substituent having the general formula $R^4 OH$ wherein $R^4$ is a divalent hydrocarbon group, said organopolysiloxane having a viscosity range of 1 to 100,000 centistokes at 25° C. and a carrier selected from the group consisting of an aqueous solution, an emulsion and an organic solvent.

2. A hair grooming composition as defined in claim 1 wherein the organopolysiloxane has at least one alkylamino substituent and at least one polyoxyalkylene substituent, said organopolysiloxane having a viscosity range of 5 to 10,000 centistokes at 25° C. and being a straight chain.

3. A hair grooming composition as defined in claim 2 wherein $R'$ is an alkylene group, a has a value of 0 to 1, $R^4$ is an alkylene group, b is 1, m has a value of 2 to 3, and c has a value of 3 to 70.

4. A hair grooming composition as defined in claim 3 wherein $R'$ is propylene.

* * * * *